United States Patent [19]
Sankaram et al.

[11] Patent Number: 5,856,526
[45] Date of Patent: Jan. 5, 1999

[54] PESTICIDAL DRY POWDER FORMULATION ENRICHED IN AZADIRACHTIN UP TO 88% AN EMULSIFIABLE CONCENTRATE ENRICHED UP TO 30% OF AZADIRACHTIN AND A PROCESS FOR PREPARING SUCH FORMULATION AND CONCENTRATE FROM NEEM SEED/KERNEL

[76] Inventors: Akella Venkata Bhavani Sankaram; Madugula Marthandamurthi; Dattatreya Manohar Akkewar; Vedala Srinivasa Singari Ramgopal; Mukkamala Subramanyam; Voruganti Srihari; Tiruchirapally Natesan Parthasarathy; Attaluri Narasimha Rao; Jayanti Venkata Suryanarayana Murthy; Mohammed Abdul Muneem, all of c/o Indian Institute of Chemical Technology, Hyderabad—500 007, Andhra Pradesh, India

[21] Appl. No.: 726,297

[22] Filed: Oct. 2, 1996

[30] Foreign Application Priority Data

Oct. 19, 1995 [IN] India .............................. 1919/DEL/95

[51] Int. Cl.$^6$ .......................... C07D 321/12; A01N 43/02
[52] U.S. Cl. ........................... 549/348; 514/450; 504/291
[58] Field of Search .................................... 549/381, 349; 514/453, 450; 504/292, 291; 424/195.1

[56] References Cited

PUBLICATIONS

K.J. Feuerhake, "Effectiveness and Selectivity of Technical Solvents for the Extraction of Neem Seed Components with Insecticidal Activity," Proc. 2nd Int. Neem Conf., Rauischholzhausen, 1983, pp. 103–114.

H.C. Sharma, K. Leuschner, A.V.B. Sankaram, D. Gunasekhar, M. Marthandamurthi, K. Bhaskariah, M. Subramanyam, N. Sultana, "Insect Antifeedants and Growth Inhibitors from Azadirachta Indica and Plumbago Zeylanica," Proc. 2nd Int. Neem Conf., Rauischholzhausen, 1983, pp. 291–320.

J.H. Butterworth and E.D. Morgan, "Isolation of a Substance that Suppresses Feeding in Locusts", Chemical Communications, 1968, pp. 23–24.

Isao Kubo and James A. Klocke, "Azadirachtin, Insect Ecdysis Inhibitor," Agric. Biol. Chem. 46 (7), 1982, pp. 1951–1953.

M. Jacobson, "Neem Research in the U.S. Department of Agriculture: Chemical, Biological and Cultural Aspects," Proc. 1st Int. Neem Conf., Rottach–Egern, 1980, pp. 33–42.

J.H. Butterworth and E.D. Morgan, "Investigation of the Locust Feeding Inhibition of the Seeds of the Neem Tree, *Azadirachta Indica*," T. Insect Physiol., vol. 17, 1971, pp. 969–977.

R.B. Yamasaki, J.A. Klocke, S.M. Lee, G.A. Stone and M.V. Darlington, "Isolation and Purufication of Azadirachtin from Neem (*Azadirachta indica*) Seeds Using Flash Chromatography and High–Performance Liquid Chromatography," Journal of Chromatography 356 (1986), pp. 220–226.

D.R. Schroeder and K. Nakanishi, "A Simplified Isolation Procedure for Azadirachtin,", Journal of Natural Products, vol. 50, No. 2, Mar.–Apr. 1987, pp. 241–244.

*Primary Examiner*—Amelia Owens
*Attorney, Agent, or Firm*—Lowe Hauptman Gopstein Gilman & Berner

[57] ABSTRACT

The invention relates to a preparation of azadirachtin, in a dry solid powder form, having a purity upto 88%; an emulsion concentrate having upto 30% by weight of azadirachtin, and a process for preparing said azadirachtin dry powder from neem seeds/kernels, which comprising: (a) disintegrating the neem seeds/kernels into a powder; (b) subjecting the said powder to continuous extraction using methanol or aqueous methanol or ethanol (rectified spirit) or aqueous ethanol at ambient temperature; (c) concentrating the extract and stirring the concentrate with petroleumether or hexane and phase separating by conventional methods; (d) stirring the denser phase containing major quantity of azadirachtin with a water immiscible organic solvent and water as required depending on the solvent used for extraction and phase separating by conventional methods; (e) concentrating the organic phase and gradually adding the concentrate to petroleumether or hexane under stirring at ambient temperature (f), filtering under suction and drying under vacuum at a temperature in the range of 25°–65° C. to obtain a neem seed/kernel extract as a powder having azadirachtin of 10–19% purity; (g) redissolving the product obtained in step (f) in a solvent and adding the solution to petroleumether or hexane at ambient temperature gradually under stirring yielding a white solid, which after filtration and drying under vacuum at 65° C. resulting in azadirachtin having 15–26% purity as a white powder (h), dissolving the azadirachtin (10–19%) from step (e) in an organic solvent and subjecting to column chromatography silicagel) by stepwise elution using different compositions of hexane/petroleumether and ethylacetate leading to solid azadirachtin powder upto 49% (i) dissolving the azadirachtin having upto 49% purity in methanol, ethanol or acetonitrile and subjecting it to HPLC (C18 column) to produce azadirachtin of purity upto 88% in a solid powder form, and (j) and stirring the product of step (i) with solvents and emulsifiers with or without synergist and UV stabiliser to obtain the emulsifiable concentrate.

18 Claims, 1 Drawing Sheet

Fig. 1

PESTICIDAL DRY POWDER FORMULATION ENRICHED IN AZADIRACHTIN UP TO 88% AN EMULSIFIABLE CONCENTRATE ENRICHED UP TO 30% OF AZADIRACHTIN AND A PROCESS FOR PREPARING SUCH FORMULATION AND CONCENTRATE FROM NEEM SEED/KERNEL

The present invention relates to an azadirachtin preparation in the form of dry solid powder having purity upto 88%, an emulsifiable concentrate comprising upto 30% by weight of azadirachtin and a process for producing such dry solid azadirachtin preparation and emulsifiable concentrate directly from neem seeds/kernels. The dry solid azadirachtin powder prepared by the process of this invention is suitable for insect pest control formulations for use in Agriculture, Veterinary and Public Health from neem (Azadirachta indica A. Juss) seeds/kernels. The concentrate prepared by the process of the invention is also used directly as insect pest control agent.

Figure 1:
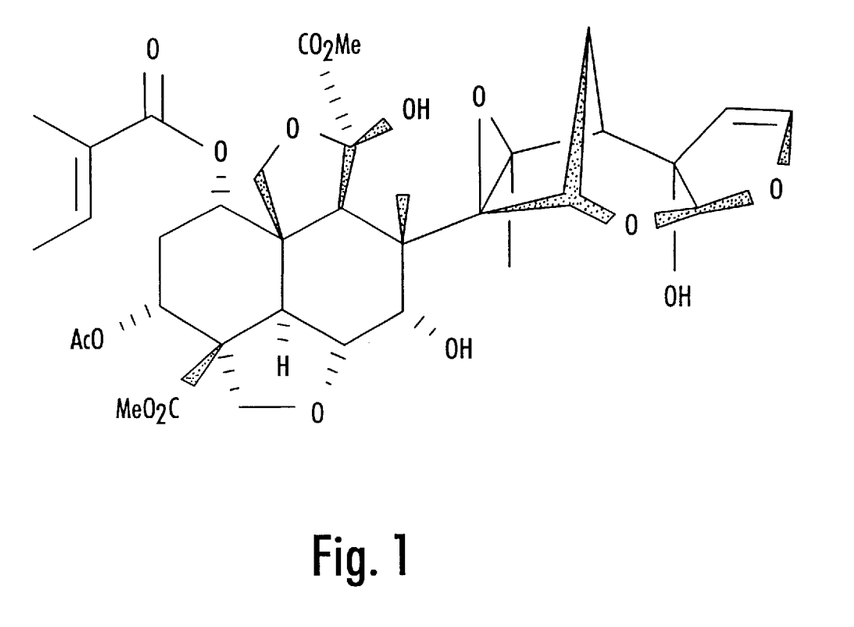

Azadirachtin has structure shown in FIG. 1 of the drawing accompanying this specification. Azadirachtin has been termed as "Azadirachtin A" subsequently, since a number of related compounds designated "Azadirachtins (B-I)" and "Azadirachtin K" have been isolated by different groups (Rembold, H., in Economic and Medicinal Plant Research; Eds., Govindachari, T. R., Sandhya, G. and Ganeshraj, S. P., Indian Journal of Chemistry, 31A, 295, 1990; Wagner. H. and Norman, R., Academic Press. New York, 3, 7, 1990; Govindachari, T. R., Sandhya, G., Ganeshraj, S. P., Journal of Natural Products, 55, 596, 1992).

There are several broad spectrum highly toxic organic synthetic insecticides currently in use, for the control of insect pests of food and commercially important crops. Besides, effectively controlling the target pests, they also destroy the natural enemies of pests and other beneficial insects. Insects also develop resistance to some of them owing to indiscrete use. There are also instances of toxic effects of residues of some of the synthetic insecticides for the consumers of the product due to poor biodegradability. Therefore, there is a need for environmentally compatible insecticides possessing activity at low concentrations and selective toxicity to insect, pests, low toxicity to plants and mammals, desired stability and economic viability.

Neem trees are widely distributed in India and some regions of Asia, Africa and Australia. Neem leaves, neem seeds, neem oil and neem cake are traditionally used in India from a long time for insect pest control. Of these, neem seeds constituting an annually renewable natural source, are associated with highest insect pest control properties.

There are numerous examples reporting the insect antifeedant and insect growth inhibitory properties of azadirachtin for a variety of insect pests (For examples, Butterworth, J. H. and Morgan, E. D., J. Chem. Soc. Chem. Communs. 23, 1968; Leuschner, K., Naturwissenschaften, 59, 217, 1972; Ruscoe, C. N. E., Nature, Lond., 236, 466, 1972; Schmutterer, H. and Rembold, H., Z, Angew. Ent. 2, 179–188, 1980; Warthen, J. D. Jr., ARMNE-4 USDA, SEA, Agricultural Reviews AND Manuals, 1979; Kubo, I. and Klocke, J. A., Agricultural and Biological Chemistry, 46, 1951, 1982; Champagne, D. E., Koul, O., Isman, M. B., Scudder, G. E. and Towers, G. H. N., Phytochemistry, 31, 377, 1992).

Azadirachtin has also been reported to be non mutagenic (Jacobson, M., Proceedings of the First International Neem Conference, Rottach Egern, 33, 1980; in Natural pesticides from the neem tree, Azadirachta indica A. Juss, Schmutterer, H., Ascher, K. R. S., Eds., German Agency for Technical Cooperation, Eschborn, Germany, 1981) and it appears to have no apparent mammalian toxicity (Nakanishi, K., Recent Advances in Phytochemistry, 5, 283, 1975; Morgan, E. D., Proceedings of the First International Neem Conference, Rottach-Egern, 43, 1980; in Natural pesticides from neem tree, Azadirachta indica A. Juss, Schmutterer, H., Ascher, K. R. S., Rembold, H., Eds., German Agency for Technical Cooperation, Eschbom, Germany, 1981).

As a result of the above studies, azadirachtin has been considered to be a promising environmentally compatible insect pest control against for plant protection. It has not come to commercial use because it is expensive to isolate it in a pure form from the neem seed/kernel extract and it is a very complex molecule for an economical chemical synthesis. Azadirachtin has also been found to degrade rapidly due to environmental factors such as UV radiation in sunlight, heat, air moisture, acidity and enzymes present in foliar surfaces (Sundaram, K. M. S. and Curry, J., Journal of Pesticide Science, 41, 129, 1994).

Several groups have investigated the insect antifeedant and insect growth inhibitory properties of solvent extracts of neem seeds or kernels against various insect pests in the laboratory and for the protection of a number of crops against their insect pests under field conditions as they are relatively less expensive and more stable in comparison with pure azadirachtin, leading to promising results (For Examples, Schmutterer, H., Ascher, K. R. S., Rembold, H., Eds., Natural pesticides from the neem tree, Azadirachta indica A. Juss, German Agency for Technical Cooperation, Eschborn, Germany, 1981, 297 pp, Proceedings of the 1st International Neem Conference, Rottach-Egern, 1980; Schmutterer, H., Ascher, K. R. S., Eds., Natural Pesticides from the neem tree, Azadirachta indica A. Juss and other tropical plants, 583 pp, German Agency for Technical Cooperation, Eschborn, Germany, 1984; Proceedings of the 2nd International Neem Conference, Rauischholzhausen, 1983; Schmutterer, H., Ascher, K. R. S., Eds., Natural pesticides from neem tree, Azadirachta indica A. Juss, and other tropical plants, Germany agency for Technical Cooperation, Eschborn, Germany, 703 pp, 1987; Proceedings of Third International Neem Conference, Nairobi, 1986).

However, solvent extracts of neem seeds or kernels are rather complex mixtures of several compounds requiring standardisation with respect to azadirachtin for reproducible biological activity and performance against insect pests under field conditions. In the prior art, a number of solvents and different temperatures have been explored for extraction of azadirachtin from neem seeds/kernels. Some of these processes are referred below for information.

In the prior art, Butterworth and Morgan (Butterworth, J. H. and Morgan, E. D., J. Insect Physiol., 17, 969, 1971) prepared azadirachtin from neem seeds (2 kg). involving (1), extraction with ethanol (170 g.); (2), partition of the concentrate of ethanol extract between methanol and light petroleum; (3), chromatography (Floridin earth) of partition product (70 g.) from methanol phase leading to azadirachtin containing fractions (2 g.); (4), preparative layer chromatography (PLC) of azadirachtin containing fractions from step 3 resulting in azadirachtin (1.5 g.). The product obtained from step 2 in this process (76 g.) would be economical to obtain but it would be viscous and oily due to the presence of water soluble compounds and therefore, it is not suitable for preparing good formulations; requiring further processing by less expensive techniques for the preparation of a dry powder enriched in azadirachtin.

In the prior art, Uebel, Warthen, Jr. and Jacobson (Uebel, E. C., Warthen, Jr. J. D. and Jacobson, M, J. Liq. Chromatogr., 2, 878, 1979) have isolated azadirachin (2 kg. batches, 90% purity, 8.7 g.) from neem seeds/kernels (48.2 kg.) involving the following steps (1), grinding neem seeds/ kernels (2 kg. batches) in hexane in a Waring blender, filtration of the homogenate to give a residue (marc); (2), soxhlet extraction of powdered marc (1.1 kg. batches) with acetone (24 h.); (3), washing of acetone extract with (a) hexane, (b), water and (c), hexane; (4), treatment of washed acetone extract with 70/30, 75/25, methanol/water; (5), treatment of 70/30, 75/25 methanol/water soluble parts with 75/25, diethylether/acetone to give 75/25, diethylether/ acetone soluble azadirachtin containing fractions (102.8 g.); (7), chromatography (Phase-bonded C-18, Hi-florisil) of diethylether/acetone fractions leading to azadirachtin (8.7 g. 90% purity). The product obtained after treatment of acetone extract with 70/30, 75/25, methanol/$H_2O$ at step 5 by this process requires modification, avoiding diethylether a highly inflammable solvent and difficult for solvent recovery and repetitive use in large scale operations. Furthermore, the process details require greater simplification in steps (1), (2) and (3) for large scale operations such as, pre-extraction of neem seed kernels with hexane, before extraction with acetone, should also be avoided since azadirachtin is unstable at the boiling point of acetone (57° C.) compared to ambient temperature. Acetone is a low boiling solvent and it is also not an excellent solvent for recovery and repetitive use in large scale operations economically. This method is therefore, not well suited for producing enriched dry azadirachtin powder because the operations are too many, hazardous, uneconomical and inconvenient for large scale preparations.

In the prior art, Feurhake (Feuerhake, K. J., Proceedings of Second International Neem Conference, Rauischholozhausen, 103, 1983; in Natural Pesticides from the neem tree and other Tropical plants, Schumutterer, H. and Ascher, K. R. S., Eds., German Agency for Technical Cooperation, Eschborn, Germany, 1984), investigated the suitability of the technical solvents (a), methyl tertiary butyl ether (MTB); (b), methyl isobutyl ketone (MIK); (c), methyl ethyl ketone (MEK); (d), water; (e), methanol; (f), azeotropic mixture of methanol and MTB, (AZT); (g), acetone and (h), butanol and they have recommended AZT for the preparation of azadirachin enriched extracts and found that water is not a convenient solvent for extracting azadirachin since its solubility in water is low. Use of neem oil and p-aminobenzoic acid for protection of azadirachtin is also a prior art. Some examples of other commercial formulations based on neem seeds/kernels/oil are Azatin, Neemguard which is a neem oil formulation, Neemgold containing 300 ppm azadirachtin and Neemazal F.

The procedure consists of the following steps; (1), ground neem seed kernels were first extracted in a soxhlet with petroleum ether to remove fatty matter; (2), the extraction was continued with solvents such as MIBK and MTB or acetone or MeOH or AZT or MEK or butanol for 10 h.; (3), the residue from AZT extract after removal of the solvent was treated with methanol; (4), the methanol soluble portion from step 3, was subjected to liquid-liquid extraction with methanol 50% and light petroleum giving rise to AZT-VR-NR in a yield of 1–1.5% which is expected to be enriched in azadirachtin.

It is desirable to avoid pre-extraction of neem seed kernels with petroleum ether and avoid extraction in a soxhlet with polar solvents at high temperature, since, azadirachtin is not quite stable at these temperatures. In this process, the physical state and stability of AZT-VR-NR were not defined. It will be the starting point for the preparation of a dry solid-enriched in azadirachtin suitable for formulations.

The U.S. Pat. No. 4,556,562, (Larson, R. O., 1985) involves extraction of neem seed kernel powder with ethanol at 60°–90° C. to give ethanol extract containing 5,000–10,000 ppm of azadirachtin which was treated with nonionic emulsifier and diluted to 2,000–4,000 ppm of azadirachtin in the pH range 3.5–6 and p-aminobenzoic acid and neem oil as stabilisers. Extraction of neem seeds with ethanol has been carried out earlier by Butterworth and Morgan for the isolation of azadirachtin (Butterworth, J. H. and Morgan, E. D., J. Insect Physiol., 17, 969, 1971). Sankaram and coworkers have obtained a fraction enriched in azadirachtin from ethanol extract of defatted neem seeds (soxhlet), dissolved it in acetone, treated it with emulsifier Teepol and diluted it to 0.1% with water and the resulting formulation protected sorghum and pearl millet crops against their insect pests (Sharma, H. C., Leuschner, K., Sankaram, A. V. B., Gunasekhar, D., Marthandamurthi, M., Bhaskariah, K., Subrahmanyam, M. and Sulthana, N., Proc. 2nd Int. Neem Conf. Rauischholzhausen, 291, 1983; in Natural Pesticides from the neem tree, Eds., Schmutterer, H., Ascher, K. R. S., German Agency for Technical Cooperation, Eschborn, Germany, 1984).

Yamasaki, Klocke, Stone and Darlington (Yamasaki, R. B., Klocke, J. A., Stone, G. A. and Darlington M. V., J. Chromatogr. 18, 467, 1986) have isolated azadirachtin from neem seeds (1 kg.) to obtain azadirachtin (56 mg., 99% purity) involving the following steps; (1), neem seeds suspended in hexane (21.) were stirred occasionally at ambient temperature for several hours and the hexane extract was decanted and the process was repeated three more times; (2), the defatted marc from step 1 was extracted six times with methanol (21.) successively, in the same manner as with n-hexane; (3), the filtrate of combined methanol extracts was concentrated in vacuo to give an orange tar (78 g.); (4), the orange tar from step 4 was redissolved in methanol (21.) and diluted with distilled water (21.) under stirring; (5), the aqueous methanol mixture from step 4 is extracted three times with equal portions of n-hexane followed by three equal quantities of dichloromethane; (6), the combined dichloromethane extract is subjected to flash chromatography (Silicagel, eluent, diethylether/methanol) to give amorphous azadirachtin (7.3%, 7.4 g.), as an orange solid. However, its stability and its suitability for pesticidal applications have not been explored; azadirachtin (7.3%) has been enriched further to azadirachin (26%, yield; 1.26 g.) by flash chromatography (ODS column, mobile phase, methanol/$H_2O$, 3/2). The physical state and stability of azadirachtin (26%) have also not been explored; (8), azadirachin (26%) from step 7 is subjected to preparative HPLC to give azadirachin (70%) (silicagel, isopropanol/n-hexane 1/3, yield: 0.280 g.); (8), azadirachin (70%) was subjected to phenyl preparative HPLC to give azadirachtin (99%, mobile phase, acetonitrile/$H_2O$, 3/7, yield; 56 mg.). Although, this procedure can be used for preparation of azadirachtin (5–30%) suited for pesticidal applications it involved (1), stirring occasionally, ground neem seeds in hexane for several hours and repeating again three times with hexane, six times with methanol decanting everytime, successively and this procedure is not convenient and economical for large scale operations and it requires drastic revision; (2), defatting of neem seeds in step 2 with hexane has to be eliminated if possible, since it can reduce the extraction time and cost of production of azadirachtin.

In this process, azadirachtin (7.3%) orange solid, yield 0.74%) obtained by flash chromatography (silicagel) of dichloromethane extract in step 4 is a candidate for novel formulations; however, flash chromatography is an expensive procedure and the yield is low. It is desirable to optimise the purification of dichloromethane extract obtained after step 5 avoiding chromatography leading to a dry solid powder enriched in azadirachtin in a superior yield. It is also desirable to avoid a low boiling environmentally incompatible solvent like dichloromethane. Solvent recovery is poor for large scale operations. Substantially, this procedure is not suited for economic production of solid azadirachtin powder suitable for pesticidal formulations.

Schroeder and Nakanishi (Schroeder, D. R. and Nakanishi, K., J. Nat. Prod., 50 242, 1987) have described isolation of azadirachtin from neem seed kernels involving the following steps; (1), neem seed kernels (2.0 kg.) were ground with hexane (21.) in a commercial Waring blender (10 min.) to a fine powder and allowed to settle for 1 h., agitated again and filtered under vacuum to give a neem seed kernel extract residue; (2), the procedure described in step 1 is repeated four times successively resulting in a defatted neem seed kernel cake which is extracted with 95% ethanol (21.), five times by the procedure described in step 1 by percolation within the blendor for 8–12 h.; (3), the combined ethanol extracts after concentration in vacuum yielded a dark viscous residue (185 g.); (4), the ethanol extract residue from step 3, was partitioned betveen hexane and methanol/$H_2O$, 95/5; (5), the 95/5 methanol/water phase (138 g.) was partitioned with water and ethyl acetate successively; (6), the ethylacetate phase (59 g.) was subjected to silica gel filtration with ethylacetate to give a product (52 g.) enriched in azadirachtin; (7), the product (52 g.) from step 6 was subjected to vacuum liquid chromatography (EtOAc/hexane, 3/1) yielding azadirachtin fractions (13 g.); (8) crystallisation of azadirachtin fractions from carbontetrachloride gave crude azadirachtin (8.5 g.); (9), flash chromatography of the product from step 8 ($CHCl_3/CH_3CN$, 3/1) gave azadirachtin (5 g.). Extraction by grinding of neem seed kernels with hexane and ethanol in a Waring blender as described in this procedure is hazardous, uneconomical, and inconvenient for the large scale preparation of azadirachtin requiring modifications. In this procedure, the residue from ethylacetate extract in step 6 (52 g.) is the starting point for preparation of dry solid enriched in azadirachtin for novel formulations without losing the yield preferably, by economic solvent fractionation techniques. Defatting with hexane before extraction with 95% ethanol can be avoided. The steps silicagel filtration and vacuum liquid chromatography to get azadirachtin enriched fractions are difficult to optimise in large scale for preparation of purer azadirachtin required for novel pesticide formulations and it requires modification. The procedure is not suited for large scale operations.

EP 0311 284, A2 (1988) reports a procedure for the preparation of azadirachtin (25% yield; 0.25%) as a pale yellow residue for the preparation of hydrogenated azadirachtin as an insecticide. This procedure has too many time consuming and uneconomic operations and the yield of the desired product is low. It has to be simplified and optimised to convert it into a manufacturing process for dry solid enriched in azadirachtin suitable for novel formulations.

Govindachari, Sandhya and Ganeshraj (Govindachari, T. R., Sandhya, G, and Ganeshraj, S. P., Chromatographia, 31, 303, 1991) have prepared azadirachtin A involving the following steps; (1), defatting of powdered neem seed kernels (1 kg.) with hexane (31.); (2), extraction of defatted powdered neem kernels with refluxing 95% ethanol (a), (1 1.) and (b), (0.5 1.), (3), partition of ethanol concentrate (95 g.) obtained after removal of solvent from combined ethanol extract dissolved in 90% methanol with petroleum ether (100 ml.) thrice; (4), treatment of residue after removal of solvent from methanol extract from step 3, with ethylacetate; (5), washing of ethylacetate extract with water to remove proteins, carbohydrates; (6), removal of solvent from ethylacetate extract to give azadirachtin (25%, 24.5 g.); (7), preparative HPLC of azadirachtin (25%, 4 g.) on RP 18 column to give azadirachtin A+D (340 mg.); (8), preparative HPLC of azadirachtin A+D to give azadirachtin A (160 mg.).

In this procedure, the physical state of the product containing 25% azadirachtin is not defined. Furthermore, the defatting step has to be eliminated. The extraction methodology requires modification for manufacturing dry azadirachtin powder suitable for novel formulations, since azadirachtin is known to be unstable at high temperatures, extraction at refluxing temperature of ethanol has to be avoided. Refluxing of powdered neem kernels with 95% ethanol is not convenient for large scale extractions, economically. Kleeberg, reported the preparation of a stable azadirachtin rich powder from neem seeds (Kleeberg,n H., Ger. Offen. DE4, 109, 473, 1992, Chermical Abstracts, 118, 18002, s, 1993) involving (1) extraction of neem seeds with water; (2), extraction of aqueous extract with ethylacetate; (3), treatment of ethylacetate concentrate with petroleum ether resulting in enriched azadirachtin powder. This process is not suitable for preparing powder enriched in azadirachtin economically, due to the fact that water is not a suitable solvent for extraction of azadirachtin from neem seeds economically, since solubility of azadirachtin in water is very poor compared to solvents such as methanol and ethanol which extract azadirachtin from neem seeds/kernels efficiently. The yield of the azadirachtin powder will be low by this procedure.

Majority of the above processes employ initial extraction of seeds or kernels either with petroleumether/hexane/heptane. This is followed by extraction with polar solvents such as acetone or methanol or ethanol at ambient temperature or at refluxing temperature of the solvent or in a soxhlet extraction apparatus. Furthermore, these methods aim at extraction of expensive pure azadirachtin required for determination of its structure, chemistry, biological activity and analytical studies using sophisticated and elaborate, Preparative Layer Chromatography (PLC), Column Chromatography and High Performance Liquid Chromatography (HPLC) techniques, irrespective of the applicability of the intermediate stages of the extracts for their azadirachtin content, physical state, suitability for storage, stability, and for preparation of their formulations for practical insect pest control. In fact, in the above said processes, neem seed and kernel extracts fairly rich in azadirachtin content have been obtained but their physical state, suitability for storage, stability, formulation and economic production have not been explored and they are not well suited for large scale preparation economically. For storage, stability and formulation, it is desirable to have a free flowing powder containing 5–30% of azadirachtin, and for the preparation of formulations such as Emulsifiable concentrates (EC), Wettable dispersable powders (WDP), dusts, granules, aerosols, controlled release formulations etc., the extracts should be prepferably devoid of even traces of water soluble compounds such as inorganic salts, carbohydrates, proteins and colouring matters as these would present problems for example, in designing a suitable solvent for dissolution of the active ingredient for the preparation of an emulsifiable concentrate and stability for practical applications.

Viewed in this context, the concentrates of crude polar solvent extracts of neem seeds or kernels obtained after the removal of solvents by the above process are usually oily and gummy due to the presence of fatty constituents and water soluble compounds such as tannins, organic carboxylic acids, carbohydrates, proteins, organic and inorganic salts, pigments etc., and they do not possess good keeping qualities. These concentrates also present problems of solubility in the preparation of Emulsifiable concentrate (EC) formulations and caking in the preparation of Wettable dispersable powders (WDP) formulations, dusts, and granular formulations.

In spite of the above advances, there is a need for a procedure for the preparation of a neem seed/kernel extract in a dry powder form in a large scale conveniently with 5–30% of azadirachtin, stability, good solubility in organic solvents suitable for EC formulations and compatibility with carrier materials for producing WDP formulations useful for insect pest control.

Acetone solutions of azadirachtin when exposed to sunlight for seven days and sixteen days gave >50% and complete reduction respectively, in insect antifeedant activity against 1st instar fall armyworm (Spodoptera frugiperda) implicating the destruction of azadirachtin (Stokes, J. B., Redfern, R. E., J.Env. Sci.Health. Part A, 1982, A, (17), 57–65; Chemical Abstracts, 96: 137955). Photodegradation of azadirachtin in sunlight was arrested to <25% for two weeks by Neem, Angelic, Castor and Calanus oils.

Extraction of neem seeds with ethanol, isolation of azadirachtin from the ethanol extract, and insect antifeedant properties of azaidrachtin for desert locust have been reported much earlier by Butterworth and Morgan in 1971 (Butterworth, J. H. and Morgan, E. D., J. Insect Physiol. 17, 969, 1971).

Neem extracts enriched in active compounds such as azadirachtin, salannin, desacetyl nimbin and nimbin have also been formulated using surface active agents and special solvents and these were found to be effective agents and special solvents and these were found to be effective in Field and Laboratory tests (Feuerhake, K., and Schmutterer, H., Z. Pflanzen Krank Pflanzen Schutz. 1985, 92(6) 643–9, Chemical Abstracts, 104, 163705h, 1986) as insecticides.

A mixture of citronella oil, neem seed extract containing 5% of azadirachtin, triclosan, DEET, di-pr-isocinchomerate, traces of lemon grass oil and ethanol was heated at 54° C. for 14 days resulting in an insect repellent. During heating, azadirachtin disappeared and new compounds were formed (Henry, G. V., PCT Int. Appl. 91/5, 970 6th May, 1991, 13 pp. Chemical Abstracts, 118; p. 75393 h).

The azadirachtin content of an aromatic petroleum distillate solution containing 3.2% of azadirachtin and 10% of 1,2-epoxy octane, was reduced to 2.8% on storage for twenty eight days (Butler, B. J., Ellenberger, W. P, Omilinsky, B. A. PLT, Int. Appl. No.9402, 019 (Cl.AO IN43/08) 03 Feb. 1994, U.S. application Ser. No. 920,800, 28th Jul. 1992, 32 pp; Chemical Abstracts, 120, p.263865 q.

Azadirachtin has also been found to degrade rapidlydue to environmental factors such as UV radiation in sunlight, heat, air, moisture, acidity and enzymes present in foliar surfaces (Sundaram, K. M. S. and Curry, J., Pesticide Science, 1944, 41, 129). From these results it is clear that there is a need for stabilized formulations of neem seed/kernel/oil extracts containing azadirachtin for crop protection, stored grain protection and in public health.

We have observed due to our sustained research in this area, that the major quantity of azadirachtin can be extracted directly from powdered neem seeds/kernals with polar solvent such as methanol or aqueous methanol or ethanol (recified spirit) or aqueous ethanol at ambient temperature wherein the fatty oils are predominently retained with the seed/kernel residue so that initial extaction of powerded neem seeds/kernels with hexane/petroleum ether (b.p. 60°–80° C.) for the removal of fatty oils is avoided. By carrying out the extraction at ambient temperature, thermal degradation of azadirachtin during extraction is minimised.

We have found that, it is possible to disintegrate dry neem seeds/kernels to a suitable powder smoothly in the range of particle size BSS-7 (0.2 mm)-BSS-72 (2.4 mm) for the large scale solvent extraction of powdered neem seeds/kernels.

Thus, the present invention utilises directly, methanol or aqueous methanol or ethanol or aqueous ethanol for the extraction of azadirachtin from powdered neem seeds/kernels, in a column by continuous percolation. The present invention employs continuous solvent percolation at ambient temperature to avoid decomposition of azadirachtin at higher temperature and it is convenient for modular operations.

The present invention specifically, deals with the manufacture of a neem seed/kernel extract containing upto 88% of azadirachtin as a dry powder directly from neem seeds/kernels involving continuous batch extraction using methanol or aqueous methanol or ethanol or aqueous ethanol, concentration of these extracts, solvent fractionation of the concentrates, fractional precipitation at ambient temperature, column chromatography and HPLC.

The present invention also deals specifically with the preparation of emulsifiable concentrate formulation of dry powder enriched in azadirachtin upto 30% for insect/pest control application.

Accordingly, the present invention provides a process for the preparation of an extract containing upto 88% of azadirachtin from neem seeds/kernels, as a dry powder, which comprises:

(a) disintegrating the neem seeds/kernels into powder, (b) subjecting the said powder to continuous batch percolation using methanol or acqueous methanol, or ethanol (rectified spirit) or aqueous ethanol at ambient temperature in a column, (c) concentrating the extract and stirring the concentrate with petroleum ether (b.p. 60°–80° C.) or hexane and phase separating, (d) stirring the denser phase containing azadirachtin with a water immisible organic solvent and water as required depending on the solvent used for extraction and phase separating by conventional methods, (e) concentrating the organic phase and adding gradually the concentrate to petroleum ether (b.p. 60°–80° C.) or hexane under stirring at ambient temperature (f) filtering and drying under vacuum at a temperature in the range of 25°–65° C. for obtaining an extract as a powder containing 10.0–19% of azadirachtin, (g) redissolving it in organic solvent such as dichloromethane and ethyl acetate and, (h) adding the solution to petroleum ether (b.p. 60°–80° C.). or hexane under stirring and filtering the solid and drying to give a white powder containing 15–26% of azadirachtin, dissolving the azadirachtin from step (e) in an organic solvent and subjecting to open column chromatography resulting in a powder containing upto 49% which is enriched to 88% by HPLC.

Also, the present invention provides a process for the preparation of emulsifiable concentrate enriched up to 30% azadirachtin, which process comprises stirring the azadirachtin powder alongwith an organic solvent or mixtures of organic solvents, emulsifier or emulsifier combination with or without synergist, with or without UV Stabiliser. The solvents used for dissolution of powder may be selected from aromax (petroleum distillate containing aromatic compounds), 2-butanone, cyclohexanone, dimethiformamide, dimethylphthalate, dioctylphthalate, isobutanol, isobutyl methyl ketone, isopropanol, Solvent C-IX (petroleum distillate containing higher aliphatic alkanes isoalikanes, in the range $C_5, C_7, C_8, C9$ to $C_{74}$,) and xylene individually or as suitable mixtures. The emulsifier used may be selected from commercially available ionic or nonionic emulsifiers, such as, Cresolox 3409, Emulsol MAL, Emulsol 172 RH, Igesol (CABS), Ehylene oxide condensate. 10 moles. Triton X100 and Tween 80. The synergist used is iperonyl butoxide. 2-hydroxy-4-octoyloxy benzophenone is used as a UV stabiliser optionally until a brown homogeneous stable liquid is obtained. The resulting concentrate can be used as a spray fluid for insect pest control after dilution with water.

The following steps are involved in the process of the present invention:

a. Well dried Neem seeds/kernels are disintegrated to a powder of suitable size using a mill.

b. The seed/kernel powder so obtained, from step (a) is packed into a suitable column and subjected to continuous percolation with methanol or ethanol (rectified spirit) or methanol or ethanol containing 20% water at ambient temperature and the most preferred solvent is methanol.

c. The extract in step (b) is concentrated at atmospheric pressure or under vacuum and the preferred condition is under vacuum.

d. The concentrate from step (c) is stirred with an organic solvent such as petroleum ether or hexane and the two phases viz. denser phase and lighter phase are separated.

e. The denser phase obtained from step (d) containing azadirachtin is stirred with water and a water immiscible organic solvents such as benzene, 2-butanone, chloroform, dichloromethane, dichloroethane, diisopropyl ether, ethyl acetate, methyltertiarybutylether and toluene and the phases are separated. The preferred water immiscible organic solvent is ethylacetate.

When methanol or ethanol containing 20% water is used for extraction of powdered neem seed kernels use of water along with the water immiscible solvent in this step is not required.

f. The organic phase in step (e) is concentrated at atmospheric pressure or under vacuum and preferred condition is under vacuum.

g. The concentrate obtained from step (f) is added gradually to petroleumether (b.p. 60°–80° C.) or hexane under stirring or at reflux temperature and filtered to give a brownish yellow solid which is dried under vacuum at 65° C. which contains 10–19% of azadirachtin and it can be formulated for protection of several crops such as cotton, rice, groundnut, brinjal, cabbage, castor, citrus species, coffee, potato, pulses, sorghum, sugarcane, tobacco, etc. and the stored grains against their insect pests.

h. The product from step (g) is dissolved in dichloromethane or ethylacetate and the solution is added gradually to petroleum ether (b.p. 60°–80° C.) or hexane under stirring and the resulting solid was filtered and dried at 65° C. in vacuum. The resulting white powder contains 15–26% of azadirachtin. The resultant product is useful for insect pest control formulations. The most preferred solvents used in this step are ethylacetate and petroleumether (b.p. 60°–80° C.).

i. The product from step (g) is dissolved in dichloromethane/ethylacetate and subjected to open column chromotography (Silicagel) using mixtures of hexane or petroleumether (b.p. 60°–80° C.) and ethylacetate as eluents stepwise leading upto 49% azadirachtin after removal of the solvent in vacuum as a white solid.

j The product from step (i) is dissolved in methanol, filtered through a short C18 guard column and the filtrate was diluted and subjected to semi preparative HPLC (C18 column) leading to a white solid containing upto 88% of azadirachtin.

The invention also relates to a process for the preparation of Emulsifiable Concentrate comprising upto 30% by weight of azadirachtin from neem seeds/kernels, which comprises stirring the azadirachtin powder having purity upto 88% with solvents or mixtures thereof, emulsifiers or emulsifier combinations with or without synergist and with or without UV stabiliser and thereby obtaining the clear emulsifiable concentrate. The organic solvents used in the above process are aromax, 2-butanone, cyclohexanone, dimethylformamide, dimethylphthalate, dioctylphthalate, isobutanol, isobutylmethylketone, isopropanol, solvent C-IX and xylene individually or as suitable combinations. The emulsifiers used are the ones which are commercially available ionic and nonionic emulsifiers such as Cresolox 3409, Emulsol MAL, Emulsol 172 RH, Igesol, calcium alkyl benzene sulphonate (CABS), Ethylene oxide condensates (10 moles), Triton X 100, and Tween 80. The pieronyl butoxide is used as a synergist and 2-hydroxy-4-octyloxy-benzophenone is used as UV stabiliser.

Therefore, the present invention provides an economical and convenient process for the manufacture of neem seed/kernel extract containing upto 88% azadirachtin from neem seeds/kernels directly by continuous solvent percolation at ambient temperature, by solvent extraction, concentration, solvent partition, fractional precipitation, as a dry powder suitable for formulation of Emulsifiable concentrates, Wettable dispersible powders, dusts etc, for practical insect pest control. The present invention also provides a process for enrichment of azadirachtin powder (10–26%) by stepwise column chromatography (silicagel) to azadirachtin upto 49% powder which is further enriched to azadirachtin (88%) powder by HPLC (C18 column) for special applications.

We have observed that it is not necessary to extract pulverised neem seeds or kernels first with petroleumether or hexane followed by extraction with methanol or aqueous methanol or ethanol or aqueous ethanol for the extraction of azadirachtin as the fatty oils are not extracted by these solvents at ambient temperature significantly from the powdered neem seeds and kernels and they are in fact, retained predominently with the residual seed or kernel powder and they do not interfere with the isolation of azadirachtin in subsequent stages.

In the prior art, the concentrated polar solvent extract yielded oily or gummy solid, or viscous mass even after comparable purification steps with lesser content of azadirachtin. The present process, an extract containing upto 88% of azadirachtin is obtained in the form of powder which can be easily used for preparing insect pest control formulations.

Extraction of azadirachtin by continuous solvent percolation directly with a polar solvent in a column packed with suitably disintegrated neem seeds/kernels at ambient temperature by the present economical and conveniently upscalable process is an improvement over the processes of prior art, which utilise hazardous, uneconomic and not conveniently upscalable, repititive operations such as, disintegration and extraction of neem seeds/kernels suspended in volatile and hazardous organic solvents using commercial blenders and stirring. Continuous solvent percolation of disintegrated neem seeds/kernels directly, with a polar solvent carried out economically avoiding defatting in the present economic and conveniently upscalable process at ambient temperature retaining majority of lipid constituents interfering with the extraction and enrichment of azadirachtin with the residual neem seed/kernel powder is an improvement over some of the processes of prior art, which compulsorily used avoidable solvent extraction of neem seeds/kernels, with petroleumether/hexane for defatting prior to extraction with polar solvents for the isolation of azadirachtin.

Extraction of azadirachtin at ambient temperature in the process of the present invention arresting degradation of azadirachtin due to its known thermal instability is an improvement over extractions carried out at higher temperature or in a soxhlet extraction equipment at the boiling point of the solvents used in the prior art processes. Preparation of azadirachtin powder from crude polar solvent extract of neem seeds/kernels containing azadirachtin in the process of present invention avoids expensive and unnecessary repititive operations for the preparation of similar extracts of prior art. Preparation of azadirachtin (15–26%) powder suitable for formulations by gradual addition of concentrate of ethylacetate extract to petroleumether (b.p. 60°–80° C.)/hexane under stirring followed by filteration and drying of precipitated azadirachtin powder in two successive operations by the present economical and conveniently upscalable process is an improvement over the processes of prior art which employed expensive, time consuming and some avoidable solvent extraction and partition operations, chromatographic techniques and hazardous solvents such as diethylether for the preparation of similar products.

The present process is an improvement over a procedure described in the patent Ger. Offen. Der, 109, 473 (1992) for the preparation of stable azadirachtin rich insecticidal powder from neem seeds (Kleeberg, H., Chemical Abstracts, 118, 18, 0002, s) involving (1), extraction of neem seeds with water; (2), extraction of aqueous extract with ethylacetate; (3), precipitation of azadirachtin powder from the ethylacetate concentrate by addition of petroleum ether, since the yields of the final product are expected to be low in view of poor solubility of azadirachtin in water.

Enrichment of azadirachtin (10–26%) powder to azadirachtin upto 49% powder by the present process involving stepwise elution with different compositions of petroleumether and ethylacetate by column chromatographby is an improvement over the prior art which utilised hazardous solvents such as diethylether or repeated employment of expensive chromatographic techniques.

Enrichment of azadirachtin upto 49% powder to azadirachtin (88%) according to the process of the present invention by a single easily repeatable HPLC step (C18 column) (due to the removal of undesirable polar constituents deteriorating the column in earlier steps) is an improvement over the prior art, which involves laborious PLC, which is not upscalable, time consuming solvent partition operations and hazardous solvents such as diethylether, and number of expensive chromatographic experiments.

According to the process of the present invention azadirachtin having different purities in a dry powder form which is suitable for pesticidal formulation is obtained. Further, the dry powder so obtained is stirred with organic solvents or their derivatives, emulsifiers or their combinations, UV stabiliser and synergist (optionally).

The invention is described with reference to the examples given below which are given to illustrate the invention and therefore should not be considered to limit the scope of the invention.

EXAMPLE 1

Well cleaned dry neem seeds were pulverised in a multi mill to a voarse powder having particle size ranging from BSS-7 (0.2 mm.) to BSS-72 (2.4 mm). The resulting neem seed powder (200 g.) was packed into a glass column and extracted continuously by percolation of methanol at ambient temperature. The methanol extract (1000 ml.) was concentrated at atmospheric pressure. The concentrate (40 ml.) was stirred with an equal volume of petroleum ether (b.p. 60°–80° C.) in a stirred vessel and allowed to settle. The two phases were separated in a phase separator. The denser phase was stirred with ethylacetate (40 ml.) and water (20 ml.) in a stirred vessel, allowed to settle and the lighter ethylacetate phase was separated. The denser phase was again stirred with ethylacetate (20 ml.) and processed in the same manner to give the ligher phase. Both the lighter phases were combined and concentrated at atmospheric pressure. The concentrate so obtained was gradually added to petroleum ether (b.p 60°–80° C.) (40 ml.) under stirring at room temperature or under refluxing conditions and the solid was filtered under suction and dried in vacuum (65° C.) leading to brownish yellow solid (3.65 g.) containing 10.84% of azadirachtin by HPLC analysis.

The product containing 10.84% of azadirachtin (8 g.) was dissolved in ethylacetate and the solution was applied to a column packed with silica gel (240 g. less than 0.08 mm.), slurry made with a composition of petroleumether (b.p. 60°–80° C.)/ethylacetate (9/1). The column was eluted successively with different compositions of petroleumether (b.p. 60°–80° C.)/ethylacetate starting from 9/1, 8/2, 7/3, 6/4, 5/5, 4/6, 3/7, 2/8, 1/9 and ethylacetate stepwise and fractions containing 600 ml. each were collected. Fraction 8 eluting with petroleum ether/ethylacetate composition (2/8) yielded a white residue (1.5 g.) after removal of the solvent under vacuum and it contained 30.42% of azadirachtin by HPLC.

The solid containing 30.42% of azadirachtin (500 mg), was dissolved in methanol (5 ml.) and filtered through a short column (Adsorbsil, LC, C18, 100/200 mesh) and the filtrate was made upto 10 ml. It was processed by semi-preparative HPLC ($\mu$ bondapak, C18 column (ID)×150 mm. using mobile phase—MeOH/$H_2O$. 6/4 O D range—2 AUF: Detector—UV 217 nm; flow rate—4 ml/min.; sample volume—300 $\mu$l; attenuation—1). The eluant of the peak having retention time 22.6 min. was concentrated under vacuum and residue was processed leading to a white solid which was dried under vacuum at 65° C. and its azadirachtin content was 88%.

The product (1 g.) containing 10.84% of azadirachtin was enriched to a product containing 17% of azadirachtin by dissolving in ethylacetate and adding the solution gradually to petroleumether (b.p. 60°–80° C.) under stirring and the resulting solid was filtered and dried at 65° C.

EXAMPLE 2

Well cleaned dry neem seeds were pulverised in a multi mill to a coarse powder having particle size ranging from BSS-7 (0.2 mm.) to BSS-72 (2.4 mm). The resulting neem seed powder (200 g.) was packed into a glass column and extracted continuously by prcolation of ethanol (rectified spirit) at ambient temperature. The ethanol extract (1000 ml.) was concentrated at atmospheric pressure. The concentrate (40 ml.) was stirred with an equal volume of petroleum ether (b.p. 60°–80° C.) in a stirred vessel and allowed to settle. The two phases were separated in a phase separator. The denser phase was stirred with ethylacetate (40 ml.) and water (20 ml.) in a stirred vessel, allowed to settle and the ligher ethylacetate phase was separated. The denser phase was again stirred with ethylacetate (20 ml.) and processed in the same manner to give the lighter phase. Both the lighter phases were combined and concentrated at atmospheric pressure. The concentrate so obtained was gradually added to petroleum ether (b.p. 60°–80° C.) under stirring at room temperature and the solid was filtered under suction and dried in vacuum (65° C.) leading to brownish yellow solid (3.0 g.) containing 9.15% of azadirachtin by HPLC analysis.

The product containing 9.15% of azadirachtin was dissolved in ethylacetate and the solution was applied to a volumn packed with silica gel (240 g., less than 0.08 mm.,) slurry made with a composition of petroleumether (b.p. 60°–80° C./ethyl acetate (9/1). The column was eluted successively with different compositions of petroleum ether (b.p. 60°–80° C.)/ethyl acetate starting from 9/1, 8/2, 7/3, 6/4, 5/5, 4/6, 3/7, 2/8, 1/9 stepwise and fractions containing 600 ml. each were collected. Fraction 8 eluting with petroleum ether (b.p. 60°–80° C.)ethylacetate composition 2/8 yielded a white residue (1.5 g.) after removal of the solvent under vacuum and it contained 39.7% of azadirachtin by HPLC alalysis.

The solid containing 39.7% of azadirachtin (500 mg), was dissolved in methanol (5 ml.) and filtered through a short column (Adsorbsil, LC, C18, 100/200 mesh) and the filtrate was made upto 10 ml. It was processed by semi-preparative HPLC ($\mu$ bondapak, C18 column 19 mm. (ID)×150 mm. using mobile phase—MeOH/$H_2O$,. 6/4 O D range—2 AUF: Detector—UV 217 nm; flow rate—4 ml/min.; sample volume—300 $\mu$l; attenuation—1). The eluant of the peak having retention time 22.6 min. was concentrated under vacuum and residue was processed leading to a white solid which was dried under vacuum at 65° C. and its azadirachtin content was 88%.

The product (1 g.) containing 9.15% of azadirachtin was enriched to a product containing 11.8% of azadirachtin by dissolving in ethylacetate and adding the solution gradually to petroleumether (b.p. 60°–80° C.) under stirring and the resulting solid was filtered and dried at 65° C.

EXAMPLE 3

Well cleaned dry neem seeds were pulverised in a multi mill to a coarse powder having particle size ranging from BSS-7 (0.2 mm.) to BSS-72 (2.4 mm). The resulting neem seed powder (200 g.) was packed into a glass column and extracted continuously by percolation of methanol extract (1000 ml.) was concentrated at atmospheric pressure. The concentrate (40 ml.) was stirred with an equal volume of petroleum ether (b.p. 60°–80° C.) in a stirred vessel and allowed to settle. The two phases were separated in a phase separator. The denser phase was stirred with ethylacetate (40 ml.) in a stirred vessel, allowed to settle and the ligher ethylacetate phase was separated. The denser phase was again stirred with ethylacetate (20 ml.) and processed in the same manner to give the lighter phase. Both the lighter phases were combined and concentrated at atmospheric pressure. The concentrate so obtained was gradually added to petroleum ether (b.p. 60°–80° C.) under stirring at room temperature and the solid was filtered under suction and dried in vacuum (65° C.) leading to brownish yellow solid (3.9 g.) containing 11.9% of azadirachfin by HPLC analysis.

The product containing 11.9% of azadirachtin was dissolved in ethylacetate and the solution was applied to a column packed with silica gel (240 g., less than 0.08 mm.,) slurry made with a composition of petroleumether (b.p. 60°–80° C./ethyl acetate (9/1). The column was eluted successively with different compositions of petroleum ether (b.p. 60°–80° C.)/ethylacetate starting from 9/1, 8/2, 7/3, 6/4, 5/5, 4/6, 3/7, 2/8, 1/9 stepwise and fractions containing 600 ml. each were collected. Fraction 8 eluting with petroleum ether (b.p. 60°–80° C.)ethylacetate composition 2/8 yielded a white residue (1.5 g.) after removal of the solvent under vacuum and it contained 31.19% of azadirachtin by HPLC alalysis.

The solid containing 31.19% of azadirachtin (500 mg), was dissolved in methanol (5 ml.) and filtered through a short column (Adsorbsil, LC, C18, 100/200 mesh) and the filtrate was made upto 10 ml. It was processed by semi-preparative HPLC ($\mu$ bondapak, C18 column 19 mm. (ID) ×150 mm. using mobile phase—MeOH/$H_2O$,. 6/4; O D range—2 AUF: Detector—UV 217 nm; flow rate—4 ml/min.; sample volume—300 $\mu$l; attenuation—1). The eluant of the peak having retention time 22.6 min. was concentrated under vacuum and residue was processed leading to a white solid which was dried under vacuum at 65° C. and its azadirachtin content was 88%. The product (1 g.) containing 11.9.% of azadirachtin was enriched to a product containing 15.72% of azadirachtin by dissolving in ethylacetate and adding the solution gradually to petroleumether (b.p. 60°–80° C.) under stirring and the resulting solid was filtered and dried at 65° C.

EXAMPLE 4

Well cleaned dry neem seed/kernels were pulverised in a grinder to a coarse powder having particle size ranging from BSS-7 (0.2 mm.) to BSS-72 (2.4 mm). The resulting neem seed and kernel powder (200 g.) was packed into a glass column and extracted continuously by percolation of methanol at ambient temperature. The methanol extract (1000 ml.) was concentrated at atmospheric pressure. The concentrate (40 ml.) was stirred with an equal volume of petroleum ether (b.p. 60°–80° C.) in a stirred vessel and allowed to settle. The two phases were separated in a phase separator. The denser phase was stirred with ethylacetate (40 ml.) and water (20 ml.) in a stirred vessel, allowed to settle and the ligher ethylacetate phase was separated. The denser phase was again stirred with ethylacetate (20 ml.) and processed in the same manner to give the lighter phase. Both the lighter phases were combined and concentrated at atmospheric pressure. The concentrate so obtained was gradually added to petroleum ether (b.p. 60°–80° C. 40 ml.) under stirring at room temperature and the solid was filtered under suction and dried in vacuum (65° C.) leading to brownish yellow solid (4.0 g.) containing 16.16% of azadirachtin by HPLC analysis. The product containing 16.16% of azadirachtin (8 g.) was dissolved in ethylacetate and the solution was applied to a column packed with silica gel (200 g., Acme less than 0.08 mm.,) slurry made with a composition of petroleumether (b.p. 60°–80° C./ethylacetate (9/1). The column was eluted successively with different compositions of petroleum ether (b.p. 60°–80° C.)/ethylacetate starting from 9/1, 8/2, 7/3, 6/4, 5/5, 4/6, 3/7, 2/8, 1/9 stepwise and fractions containing 600 ml. each were collected. Fraction 8 eluting with petroleum ether (b.p. 60°–80° C.)ethyl acetate composition 2/8 yielded a white residue (1.5 g.) after removal of the solvent under vacuum and it contained 49.24% of azadirachtin by HPLC alalysis.

The solid containing 49.24% of azadirachtin (500 mg), was dissolved in methanol (5 ml.) and filtered through a short column (Adsorbsil, LC, C18, 100/200 mesh) and the filtrate was made upto 10 ml. It was processed by semi-preparative HPLC ($\mu$ bondapak, C18 column 19 mm. (ID)

×150 mm. using mobile phase—MeOH/H$_2$O,. 6/4; O D range—2 AUF: Detector—UV 217 nm; flow rate—4 ml/min.; sample volume—300 ul; attenuation—1). The eluant of the peak having retention time 22.6 min. was concentrated under vacuum and residue was processed leading to a white solid which was dried under vacuum at 65° C. and its azadirachtin content was 88%.

The product (1 g.) containing 16.16% of azadirachtin was enriched to a product containing 22.89% of azadirachtin by dissolving in ethylacetate and adding the solution gradually to petroleumether (b.p. 60°–80° C.) under stirring and the resulting solid was filtered and dried at 65° C.

EXAMPLE 5

Well cleaned dry neem seed and kernels were pulverised in a grinder to a coarse powder having particle size ranging from BSS-7 (0.2 mm.) to BSS-72 (2.4 mm). The resulting neem seed and kernel powder (200 g.) was packed into a glass column and extracted continuously by percolation of methanol containing 20% water at ambient temperature. The aqueous methanol extract (1000 ml.) was concentrated at atmospheric pressure. The concentrate (40 ml.) was stirred with an equal volume of petroleum ether (b.p. 60°–80° C.) in a stirred vessel and allowed to settle. The two phases were separated in a phase separator. The denser phase was stirred with ethylacetate (40 ml.) in a stirred vessel, allowed to settle and the ligher ethylacetate phase was separated. The denser phase was again stirred with ethylacetate (20 ml.) and processed in the same manner to give the lighter phase. Both the lighter phases were combined and concentrated at atmospheric pressure. The concentrate so obtained was gradually added to petroleum ether (b.p. 60°–80° C. 40 ml.) under stirring at room temperature and the solid was filtered under suction and dried in vacuum (65° C.) leading to brownish yellow solid (3.75 g.) containing 19.93% of azadirachtin by HPLC analysis. The product containing 19.93% of azadirachtin (8 g.) was dissolved in ethylacetate and the solution was applied to a column packed with silica gel (200 g., less than 0.08 mm.) slurry made with a composition of petroleumether (b.p. 60°–80° C./ethyl acetate (9/1). The column was eluted successively with different compositions of petroleum ether (b.p. 60°–80° C.)/ethylacetate starting from 9/1, 8/2, 7/3, 6/4, 5/5, 4/6, 3/7, 2/8, 1/9 stepwise and fractions containing 600 ml. each were collected. Fraction 8 eluting with petroleum ether (b.p. 60°–80° C.)/ethyl acetate composition 2/8 yielded a white residue (1.5 g.) after removal of the solvent under vacuum and it contained 45% of azadirachtin by HPLC alalysis.

The solid containing 45% of azadirachtin (500 mg), was dissolved in methanol (5 ml.) and filtered through a short column (Adsorbsil, LC, C18, 100/200 mesh) and the filtrate was made upto 10 ml. It was processed by semi-preparative HPLC (bonda pak, C18 column 19 mm. (ID)×150 mm. using mobile phase—MeOH/H$_2$O,. 6/4 sample range—2 AUF: Detector—UV 217 nm; flow rate—4 ml/min.; sample volume—300 ul; attenuation—1). The eluant of the peak having retention time 22.6 min. was concentrated under vacuum and residue was processed leading to a white solid which was dried under vacuum at 65° C. and its azadirachtin content was 88%.

The product (1 g.) containing 19.93% of azadirachtin was enriched to a product containing 26.86% of azadirachtin by dissolving in ethylacetate and adding the solution gradually to petroleumether (b.p. 60°–80° C.) under stirring and the resulting solid was filtered and dried at 65° C.

EXAMPLE 6

Well cleaned dry neem seed and kernels were pulverised in a grinder to a coarse powder having particle size ranging from BSS-7 (0.2 mm.) to BSS-72 (2.4 mm). The resulting neem seed powder (200 g.) was packed into a glass column and extracted continuously by percolation of ethanol at ambient temperature. The ethanol extract (1000 ml.) was concentrated at atmospheric pressure. The concentrate (40 ml.) was stirred with an equal volume of petroleum ether (b.p. 60°–80° C.) in a stirred vessel and allowed to settle. The two phases were separated in a phase separator. The denser phase was stirred with ethylacetate (40 ml.) and water (20 ml.) in a stirred vessel, allowed to settle and the ligher ethylacetate phase was separated. The denser phase was again stirred with ethylacetate (20 ml.) and processed in the same manner to give the lighter phase. Both the lighter phases were combined and concentrated at atmospheric pressure. The concentrate so obtained was gradually added to petroleum ether (b.p. 60°–80° C.) (40 ml.) under stirring at room temperature and the solid was filtered under suction and dried in vacuum (65° C.) leading to brownish yellow solid (2.8 g.) containing 16.06% of azadirachtin by HPLC analysis.

The product containing 16.06% of azadirachtin (8 g.) was dissolved in ethylacetate and the solution was applied to a column packed with silica gel (240 g., less than 0.08 mm.) slurry made with a composition of petroleumether (b.p. 60°–80° C./ethylacetate (9/1). The column was eluted successively with different compositions of petroleum ether (b.p. 60°–80° C.)/ethylacetate starting from 9/1, 8/2, 7/3, 6/4, 5/5, 4/6, 3/7, 2/8, 1/9 and ethylacetate stepwise and fractions containing 600 ml. each were collected. Fraction 8 eluting with petroleumether/ethylacetate composition (2/8) yielded a white residue (1.5 g.) after removel of the solvent under vacuum and it contained 45.5% of azadirachtin by HPLC alalysis.

The solid containing 45.5% of azadirachtin (500 mg), was dissolved in methanol (5 ml.) and filtered through a short column (Adsorbsil, LC, C18, 100/200 mesh) and the filtrate was made upto 10 mnl. It was processed by semi-preparative HPLC ($\mu$ bondapak, C18 column 19 mm. (ID)×150 mm. using mobile phase—MeOH/H$_2$O,. 6/4; O D range—2 AUF: Detector—UV 217 nm; flow rate—4 ml/min.; sample volume—300 ul; attenuation—1). The eluant of the peak having retention time 22.6 min. was concentrated under vacuum and residue was processed leading to a white solid which was dried under vacuum at 65° C. and its azadirachtin content was 88%.

The product (1 g.) containing 16.06% of azadirachtin was enriched to a product containing 20.44% of azadirachtin by dissolving in ethylacetate and adding the solution gradually to petroleumether (b.p. 60°–80° C.) under stirring and the resulting solid was filtered and dried at 65° C.

EXAMPLE 7

Dry neem seed extract powder (20 gm.) obtained by any one of the previous examples was slowly added to a well stirred solution of solvent C-IX (51 g.), cyclohexanone (14 g.) Triton X 100 (4.12 g.) Tween 80 (2.94 g.), Igesol, CABS) (2.94 g.) and piperonylbutoxide (5 g.) were taken in a beaker and stirring continued for 1 hr. until a clear brown solution was obtained.

EXAMPLE-8

Neem seed extract powder (1 kg.) obtained by any one of examples 1 to 6 was added slowly to a well stirred homogeneous solution of solvent C-IX (2.35 kg.) cyclohexanone (1 kg.), Triton x 100 (206.0 g.) Tween 80 (147 g.), Igesol CABS (147 g.) piperonyl butoxide (500 g.) and 2-hydroxy- 4-octyloxybenzophenone, (25 g.) taken in a beaker and stirring was continued for 8 h. until a clear brown solution was obtained.

EXAMPLE-9

Dry neem seed extract powder (20 g.) obtained by any one of examples 1 to 6, xylene (51 g.), 2-butanone (14 g.) Triton X 100 (4.12 g,), Tween 80 (2.94 g), and Igesol CABS (2.94 g.), piperonyl butoxide (5 g.) were taken in a beaker and stirred for 1 h. until a clear brown solution was obtained.

EXAMPLE-10

Dry neem seed extract powder (20 g.) obtained by any one of examples 1 to 6, dimethyl phthalate (35 g.) and cyclohexanone (30 g.), em ulsol MAL (10 g.) and piperonyl butoxide (5 g.), were taken in a beaker and stirred until a clear brown solution was obtained.

EXAMPLE-11

Dry neem seed extract powder (20 g.) obtained by any one of examples 1 to 6, cyclohexanone (70 g.) and emulsifier Creslox 3409 (10 g.) were taken in a beaker and stirred until a clear brown solution was obtained.

EXAMPLE-12

Neem seed extract power (20 g.) obtained by any one of examples 1 to 6, cyclohexanone (60 g.), dioctylphthalate (8 g.) Emulsol 172 RH (10 g.), Triton X 100 (2 g.) were taken in a beaker and stirred until a clear brown solution was obtained.

EXAMPLE 13

Neem seed extract powder (20 g.) obtained by any one of examples 1 to 6, Isobutyl methyl ketone (56 g.) dimethyl formamide (14 g.), Cresolox 3409 (10 g.), were taken in a beaker and stirred until a clear brown solution was obtained.

EXAMPLE-14

Dry neem seed extract powder (20 g.) obtained by any one of examples 1 to 6, isopropanol (70 g.) Igesol, CABS (1.43 g.) and ethylene oxide condensate, 10 moles (8.57 g.) were taken in a beaker and stirred until a brown homogeneous solution is obtained.

EXAMPLE-15

Dry neem seed extract powder (20 g.) obtained by any one of examples 1 to 6, Aromax (60 g.), cyclohexanone (10 g.) and Emulsol (172 RH) (10 g.) were taken in a beaker and stirred for 1 h. until a clear brown solution was obtained.

We claim:

1. A process for the preparation of azadirachtin, in a dry solid powder form, having a purity of up to 88% from neem seeds/kernels, which comprises;
   a. comminuting neem seeds/kernels into a powder;
   b. extracting said powder using at least one member selected from the group consisting of methanol, aqueous methanol, ethanol and aqueous ethanol at about ambient temperature to form an extract;
   c. concentrating the extract,
   d. mixing the concentrate with petroleum ether or hexane whereby causing a separation of a denser phase containing major quantity of azadirachtin and an organic phase;
   e. stirring the dense phase with a solvent selected from at least one of a substantially water immiscible organic solvent and water;
   f. concentrating the organic phase to form a concentrate;
   g. adding the concentrate to at least one solvent selected from petroleum ether or hexane at about ambient temperature to form a solution;
   h. filtering said solution under vacuum at a temperature in the range of about 25°–65° C. to obtain a powder comprising a neem seed/kernel extract comprising azadirachtin of 10–19% purity;
   i. dissolving said powder in a solvent and adding the solution to at least one of petroleum ether or hexane at ambient temperature under conditions sufficient to produce a white solid powder that, after filtration and drying under vacuum at about 65° C., produces azadirachtin having about 15–26% purity,
   j. subjecting the filtrate comprising azadirachtin dissolved in a solvent from step h. to chromatography in a column housing silica gel by stepwise elution using different compositions of hexane/petroleum ether and ethyl acetate whereby producing solid azadirachtin powder having a purity of up to about 49%; and
   k. dissolving the azadirachtin having up to 49% purity in at least one member selected from methanol, ethanol or acetonitrile and passing it through a HPLC C18 column under conditions sufficient to produce a solid powder comprising up to about 88% azadirachtin.

2. A process as claimed in claim 1 wherein the comminution of the neem seeds/kernels is sufficient to obtain a powder product having a particle size in the range of about BSS-7 to BSS-72.

3. A process as claimed in claim 1 wherein the solvent used for extraction of said comminuted neem seeds/kernels in step b. comprises methanol.

4. A process as claimed in claim 1 wherein the extract obtained in step (c) is concentrated at at most atmospheric pressure.

5. A process as claimed in claim 1 wherein the organic solvent used in step e. is at least one selected from benzene, 2-butanone, chloroform, dichloromethane, dichlorolethane, disopropyl ether, ethyl acetate, methyl-tertiary butyl ether, toluene and the like.

6. A process as claimed in claim 1 further comprising concentrating said extract from step (f) at no higher than atmospheric pressure and further comprising dissolving azadirachtin powder in step i. in petroleum ether having a boiling point of about 60°–80° C.

7. A process as claimed in claim 1 wherein the solvent used for redissolution of azadirachtin in step i. is selected from ethylacetate, and dichloromethane and the solvent used for preparation of azadirachtin powder is petroleum ether.

8. A process as claimed in claim 1 wherein the technique used for purification of azadirachtin is stepwise elution employing at least one member of the oroup petroleum ether/hexane, ethyl acetate in step j.

9. A process as claimed in claim 1 wherein the stationery phase employed in step k. in said chromatographic separation column is C18 bonded silicagel and the solvent employed for purification of azadirachtin using HPLC is a mixture of methanol and water.

10. A process as claimed in claim 1 wherein the azadirachtin powder is dried in vacuum at a temperature of about between 25°–65° C. under conditions sufficient to remove substantially all adhering solvents.

11. A neem seed/kernel extract in the form of a dry solid powder having an azadirachtin content of up to about 88%.

12. A process for the preparation of an emulsifiable concentrate comprising up to about 30% by weight of azadirachtin, which comprises stirring the azadirachtin powder, having purity of up to about 88%, with at least one organic solvent, at least one emulsifier with or without at least one synergist and with or without at least one UV stabilizer.

13. A process as claimed in claim 12 wherein the organic solvents used are at least one selected from aromax, 2-butanone, cyclohexanone, dimethylformamide, dimethylphthalate, dioctyphthalate, isobutanol, isobutylmethylketone, isopropanol, solvent C-IX and xylene.

14. A process as claimed in claim 12 wherein said emulsifier is at least one member selected from nonionic and ionic emulsifiers.

15. A process as claimed in claim 12 wherein said synergist comprises piperonyl butoxide.

16. A process as claimed in claim 12 wherein the UV stabilizer comprises 2-hydroxyl-4-octyloxy-benzophenone.

17. A pesticide comprising an emulsifiable concentrate comprising up to about 30% by weight of azadirachtin obtained from neem seeds/kernels.

18. In the method of recovering azadirachtin from need seeds or kernels that comprises:

comminuting neem seeds/kernels into a powder;

extracting said powder with a solvent;

separating a denser phase containing major quantity of azadirachtin and an organic phase;

extracting the dense phase with a solvent;

concentrating the organic phase to form a concentrate;

adding the concentrate to a solvent to form a solution;

fitering said solution to obtain a powder comprising a neem seed/kernel extract comprising azadirachtin;

dissolving said powder in a solvent to form a second solution; and admixing said second solution with a further liquid to cause precipitation of a white solid powder comprising azadirachtin;

the improvement which comprises:

extracting said initial powder with a solvent by percolation through a column;

dissolving solids comprising azadirachtin in a liquid that is not an extractant for fatty oils in need seeds and kernels;

filtering said second solution to form a filtrate, comprising azadirachtin dissolved in a solvent, and a precipitated powder comprising azadirachtin;

subjecting the filtrate to chromatographic separation whereby solid azadirachtin powder having a purity of up to about 49%; and dissolving the azadirachtin powder having up to 49% purity in a solvent and then passing the solution through a column under conditions sufficient to produce a solid powder enriched in azadirachtin up to a proportion of about 88%.

* * * * *